US00PP22940P2

(12) United States Plant Patent
Mukundan

(10) Patent No.: US PP22,940 P2
(45) Date of Patent: Aug. 7, 2012

(54) ***AGLAONEMA* PLANT NAMED 'MUKLASS'**

(50) Latin Name: *Aglaonema hybrida*
Varietal Denomination: Muklass

(75) Inventor: Parthasarathy Mukundan, Alwarpet Chennai (IN)

(73) Assignee: K.S.G.'s Farm & Nursery, Chennai (IN)

( * ) Notice: Subject to any disclaimer, the term of this patent is extended or adjusted under 35 U.S.C. 154(b) by 0 days.

(21) Appl. No.: 13/373,838

(22) Filed: Dec. 1, 2011

(51) Int. Cl.
*A01H 5/00* (2006.01)

(52) U.S. Cl. ..... Plt./376

(58) Field of Classification Search ..... Plt./376
See application file for complete search history.

*Primary Examiner* — Annette Para
(74) *Attorney, Agent, or Firm* — C. A. Whealy

(57) ABSTRACT

A new and distinct cultivar of *Aglaonema* plant named 'Muklass', characterized by its upright and outwardly arching plant habit; freely clumping habit; vigorous growth habit; relatively short internodes giving a compact, dense, full and symmetrical plant form; narrowly lanceolate leaves with greyed green-colored centers contrasting with dark green-colored midveins, margins and random markings; dark green-colored petioles; and relative tolerance to low temperatures.

1 Drawing Sheet

Botanical designation: *Aglaonema hybrida.*
Cultivar denomination: 'MUKLASS'.

BACKGROUND OF THE INVENTION

The present invention relates to a new and distinct cultivar of *Aglaonema* plant, botanically known as *Aglaonema hybrida* and hereinafter referred to by the name 'Muklass'.

The new *Aglaonema* plant is the product of a controlled breeding program conducted by the Inventor in Chamrajpet, Bangalore, India. The objective of the breeding program is to create new full, dense and compact *Aglaonema* plants with good plant vigor, interesting and unique leaf shapes and variegation patterns, resistance to pathogens and pests and tolerance to low temperatures.

The new *Aglaonema* plant is the product of a cross-pollination conducted by the Inventor on Jun. 3, 2005 of *Aglaonema hybrida* 'Silver Ribbons', disclosed in U.S. Plant Pat. No. 12,985, as the female, or seed, parent with an unnamed selection of *Aglaonema stenophyllum f. linearifolium*, not patented, as the male, or pollen, parent. The new *Aglaonema* plant was discovered and selected by the Inventor in September, 2006 as a single plant from within the resultant progeny of the stated cross-pollination in a controlled environment in Tiruporur, Chennai, India.

Asexual reproduction of the new *Aglaonema* plant by cuttings and divisions in a controlled environment in Tiruporur, Chennai, India since December, 2006 has shown that the unique features of this new *Aglaonema* plant are stable and reproduced true to type in successive generations of asexual reproduction.

SUMMARY OF THE INVENTION

Plants of the new *Aglaonema* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Muklass'. These characteristics in combination distinguish 'Muklass' as a new and distinct *Aglaonema* plant:

1. Upright and outwardly arching plant habit.
2. Freely clumping habit.
3. Vigorous growth habit.
4. Relatively short internodes giving a compact, dense, full and symmetrical plant form.
5. Narrowly lanceolate leaves with greyed green-colored centers contrasting with dark green-colored midveins, margins and random markings.
6. Dark green-colored petioles.
7. Relatively tolerant to low temperatures.

Plants of the new *Aglaonema* differ from plants of the female parent. 'Silver Ribbons', in the following characteristics:

1. Plants of the new *Aglaonema* have longer and narrower leaves than plants of 'Silver Ribbons'.
2. Leaves of plants of the new *Aglaonema* have obtuse bases whereas leaves of plants of 'Silver Ribbons' have cordate bases.
3. Plants of the new *Aglaonema* and 'Silver Ribbons' differ in leaf shape, coloration and variegation pattern.

Plants of the new *Aglaonema* differ from plants of the male parent selection in the following characteristics:

1. Plants of the new *Aglaonema* are more symmetrical and denser than plants of the male parent selection.
2. Plants of the new *Aglaonema* have broader leaves than plants of the male parent selection.
3. Leaves of plants of the new *Aglaonema* have obtuse bases whereas leaves of plants of the male parent selection have attenuate bases.
4. Plants of the new *Aglaonema* and the male parent selection differ in leaf shape, coloration and variegation pattern.
5. Plants of the new *Aglaonema* and the male parent selection differ in leaf petiole color.

Plants of the new *Aglaonema* can be compared to plants of *Aglaonema hybrida* 'White Lance', disclosed in U.S. Plant Pat. No. 11,053. In side-by-side comparisons conducted in Chamrajpet, Bangalore, India, plants of the new *Aglaonema* differed from plants of 'White Lance' in the following characteristics:

1. Plants of the new *Aglaonema* had longer, narrower and flatter leaves than plants of 'White Lance'.
2. Plants of the new *Aglaonema* and 'White Lance' differed in leaf shape, coloration and variegation pattern.
3. Plants of the new *Aglaonema* and 'White Lance' differed in leaf petiole color.

Plants of the new *Aglaonema* can also be compared to plants of *Aglaonema hybrida* 'Black Lance', disclosed in U.S. Plant Pat. No. 10,280. In side-by-side comparisons conducted in Chamrajpet, Bangalore, India, plants of the new *Aglaonema* differed from plants of 'Black Lance' in the following characteristics:

1. Plants of the new *Aglaonema* were more compact and denser than plants of 'Black Lance'.
2. Plants of the new *Aglaonema* had longer, narrower and flatter leaves than plants of 'Black Lance'.
3. Plants of the new *Aglaonema* and 'Black Lance' differed in leaf shape, coloration and variegation pattern.
4. Plants of the new *Aglaonema* and 'Black Lance' differed in leaf petiole color.

BRIEF DESCRIPTION OF THE PHOTOGRAPH

The accompanying photograph illustrates the overall appearance of the new *Aglaonema* plant showing the colors as true as it is reasonably possible to obtain in colored reproductions of this type. Colors in the photograph may differ slightly from the color values cited in the detailed botanical description which accurately describe the colors of the new *Aglaonema* plant.

The photograph comprises a side perspective view of a typical plant of 'Muklass' grown in a container.

DETAILED BOTANICAL DESCRIPTION

The aforementioned photographs and following observations and measurements describe plants grown in 25-cm containers in Miami, Fla. during the summer and autumn in a polypropylene-covered shadehouse. Plants were grown under environmental conditions and cultural practices which approximate those generally used in commercial *Aglaonema* production. During the production of the plants, day temperatures ranged from 27° C. to 37° C., night temperatures ranged from 15° C. to 26° C. and light levels averaged 1,500 foot-candles. Plants were one year old when the photographs and the detailed description were taken. In the following description, color references are made to The Royal Horticultural Society Colour Chart, 2007 Edition, except where general terms of ordinary dictionary significance are used.

Botanical classification: *Aglaonema hybrida* 'Muklass'.

Parentage:

*Female, or seed, parent.*—*Aglaonema hybrida* 'Silver Ribbons', disclosed in U.S. Plant Pat. No. 12,985.

*Male, or pollen, parent.*—Unnamed selection of *Aglaonema stenophyllum f. linearifolium*, not patented.

Propagation:

*Type.*—By cuttings and divisions.

*Time to initiate roots, summer.*—About 21 to 28 days at 25° C. to 32° C.

*Time to initiate roots, winter.*—About 30 to 40 days at 12° C. to 25° C.

*Time to produce a rooted young plant, summer.*—About 30 to 35 days at 25° C. to 32° C.

*Time to produce a rooted young plant roots, winter.*—About 45 to 60 days at 12° C. to 25° C.

*Root description.*—Fleshy, medium in thickness; off-white in color.

*Rooting habit.*—Freely branching; profuse, high density.

Plant description:

*Plant and growth habit.*—Upright and outwardly arching plant habit; freely clumping habit; relatively short internodes giving a compact, dense, full and symmetrical habit; vigorous growth habit; developing leaves initially upright, then gracefully arching outwardly with development.

*Plant height, from soil level to top of leaf plane.*—About 56 cm.

*Plant diameter or spread.*—About 88 cm.

*Stem description.*—Clumping habit: Plants of the new *Aglaonema* are freely clumping with about 42 clumps developing per plant. Aspect: Mostly upright. Strength: Strong; somewhat flexible. Diameter, at the base: About 1.8 cm. Internode length, at the base: About 1 cm. Color: Close to 147A. Cataphylls: None observed.

Foliage description:

*Arrangement.*—Alternate to whorled; simple.

*Length.*—About 27 cm.

*Width.*—About 4 cm.

*Shape.*—Narrowly lanceolate.

*Apex.*—Acuminate; straight.

*Base.*—Obtuse.

*Margin.*—Entire; very slightly undulate.

*Texture, upper and lower surfaces.*—Smooth, glabrous.

*Venation pattern.*—Pinnate.

*Color.*—Developing leaves, upper surface: Ground color, closest to 144A to 144B; main veins, margins and random markings, closest to 137A to 137B; lateral venation, same as leaf coloration. Developing leaves, lower surface: Closest to 144A; venation, close to 144A. Fully expanded leaves, upper surface: Ground color, closest to 191A, 194A and/or 194B; main veins, margins and random markings, darker than N137A; lateral venation, same as leaf coloration. Fully expanded leaves, lower surface: Closest to N137A; midvein, close to 146A; lateral venation, close to N137A.

*Petiole.*—Aspect: Mostly erect, gracefully outwardly arching with development. Length: About 10 cm. Diameter, distal: About 4 mm. Diameter, proximal, flattened: About 2 cm. Strength: Strong; flexible. Color, distal: Close to 147A. Color, proximal: Close to 147B; area adjacent to stem, close to 157A to 157C. Wing length: About 9 cm. Wing diameter, base: About 4 mm. Wing color, inner and outer surfaces: Close to 147A; towards the base, close to 147B; area adjacent to stem, close to 157A to 157C.

Inflorescence description: Inflorescence development has not been observed on plants of the new *Aglaonema*.

Disease & pest resistance: Plants of the new *Aglaonema* have not been observed to be resistant to pathogens or pests common to *Aglaonema*.

Temperature tolerance: Plants of the new *Aglaonema* have been observed to be relatively low temperature tolerant and to tolerate temperatures ranging from about 15° C. to about 40° C.

It is claimed:

1. A new and distinct *Aglaonema* plant named 'Muklass' as illustrated and described.

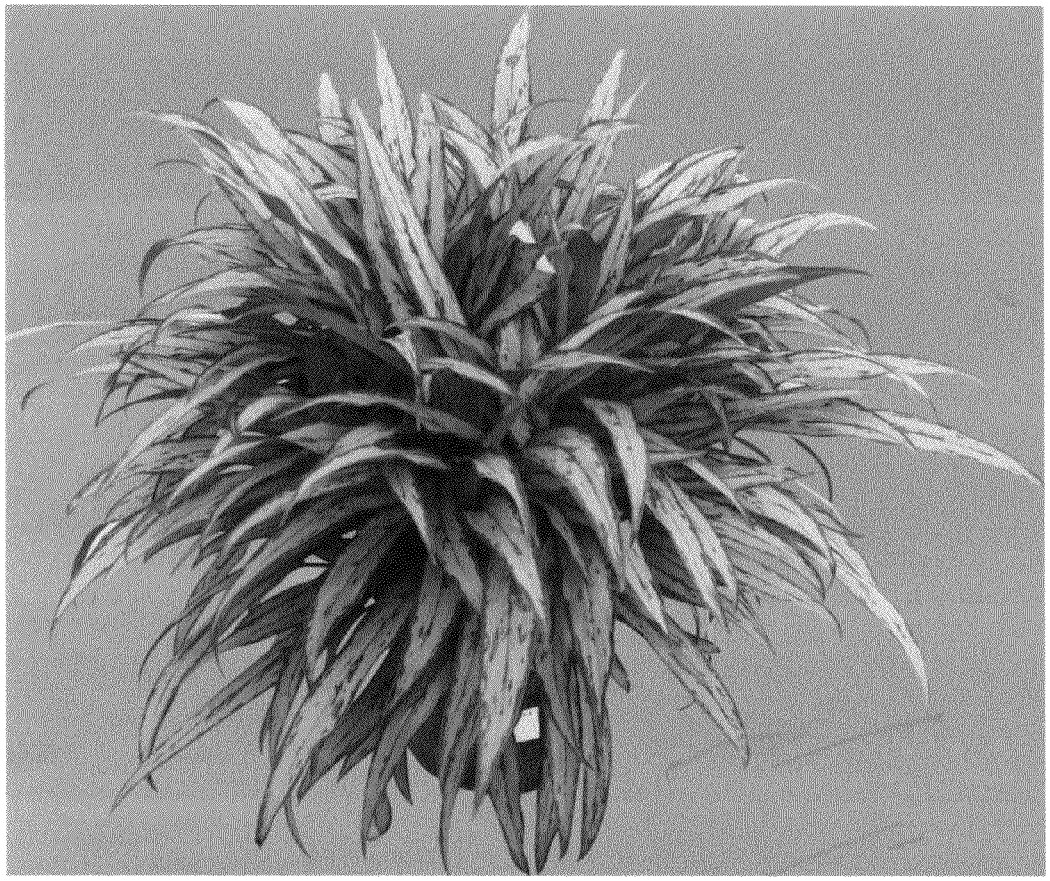

* * * * *